Sept. 24, 1974 H. WHEATCROFT Plant Pat. 3,623
ROSE PLANT
Filed July 19, 1973
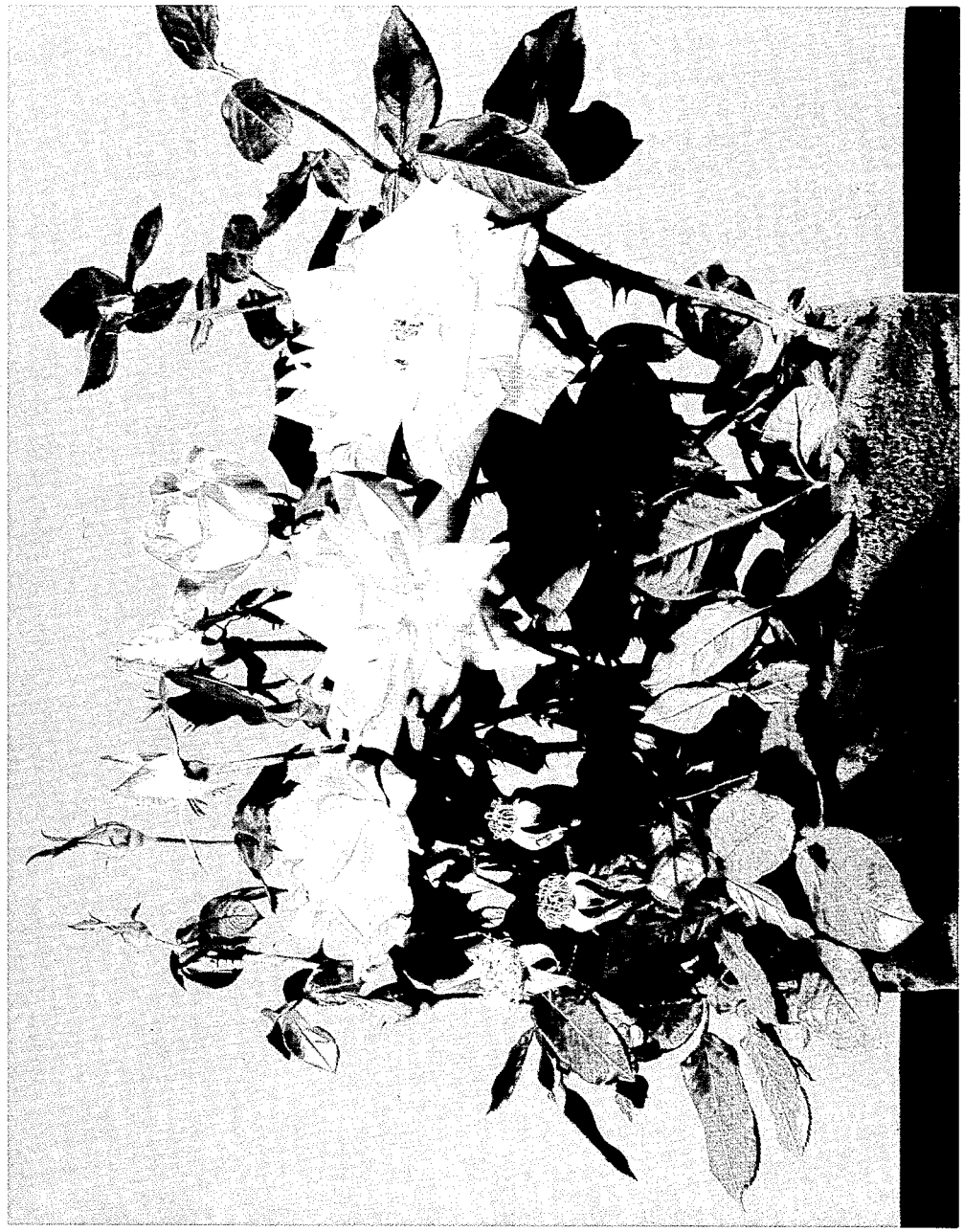

United States Patent Office

Plant Pat. 3,623
Patented Sept. 24, 1974

3,623
ROSE PLANT

Harry Wheatcroft, Edwalton, Nottingham, England

Filed July 19, 1973, Ser. No. 380,829
Int. Cl. A01h *5/00*
U.S. Cl. Plt.—13 1 Claim

ABSTRACT OF THE DISCLOSURE

A new and distinct variety of rose plant of the Hybrid Tea Class, a sport of the unpatented rose variety known as Piccadilly.

SUMMARY OF THE INVENTION

The present invention relates to a new and distinct variety of rose plant of the Hybrid Tea class which was discovered by me as a cultivated sport of the unpatented rose variety known as Piccadilly, said discovery having been made in 1966 on my rose nursery located in Edwalton, Nottingham, England.

At the time of the discovery, I was doing a routine inspection of the roses on my nursery property, and as we exhibit at many shows throughout the country of England, we are constantly going through the roses and disbudding and getting flowers for shows. On this particular inspection, one flower of the variety Piccadilly was different from all others and was so striking that I cut off the branch with this different flower and it was budded. It remained true and kept its striking flower color so we understood to build stock of this discovery. Continued observation of these budded plants conclusively established that the sport is definitely distinctive from its parent as well as other rose varieties of which I am aware.

My discovery differs from its parent in flower color by irregular stripes of bright golden yellow on the rich red color of most petals, excepting on occasion small petals and petalloids. This color variation is present in nearly every petal and is consistent from petal to petal and from flower to flower with the pattern of the yellow stripping varying from petal to petal and flower to flower. Its parent shows no variation, having an even rich red coloration on all petals. All other characteristics of my discovery are identical with its parent, including plant form, foliage, growth habit and vigor, bud form and size, as well as flower form and size.

Asexual reproduction of my new discovery by budding has been performed at Edwalton, England, and West Grove, Pa., United States of America and shows the striped color variation of the petals are established and transmitted through succeeding propagations.

BRIEF DESCRIPTION OF DRAWING

The accompanying drawing shows typical specimens of the vegetative growth and flowers of my new discovery in different stages of development and as depicted in color as nearly true as possible to make them in a color illustration of this character.

DETAIL DESCRIPTION OF DISCLOSURE

The following is a detailed description of my new variety with color terminology in accordance with the Horticultural Color Chart of the Royal Horticultural Society:

Type: Hardy; bush outdoor; sport; for garden decoration.
Class: Hybrid Tea.
Propagation: It does hold its distinguishing characteristics through succeeding propagations by budding.

FLOWER

Locality where grown: West Grove, Pa.
Flowers borne: Singly, several to stem; on normal, medium stems.

Quantity of bloom: Free, outdoors.
Continuity: Continuous.
Fragrance: Very slight; tea.
Bud: Peduncle; Medium long; medium heavy; erect; reddish green 183A; medium rough; numerous hairs; red.
- *Before calyx breaks:* Size: medium. Form: ovoid with a conspicuous neck; with foliaceous appendages on the surface of the bud; with slender medium cut foliaceous parts extending beyond the tip of the bud equal to ¾ or more of its length.
- *As calyx breaks:* Color: 11A with one petal shaded with 53A.
- *As first petal opens:* Size: medium. Form: pointed. Color: outside: 21B, one or two petals shaded or brushed with 53A to 53D; inside: base and lower part of petal 21A, upper half of petal from 46B to 46C brushed, penciled and streaked with 21A and 21B (variegated). Opening: It does open up well.

Bloom: Size when fully open: large, 4 inches to 5 inches.
- *Petalage:* Double; from 20 to 25 petals; arranged regularly.
- *Form:* Cupped at first; becoming open cupped; petals remaining at first loosely cupped rolled outward; becoming later at maturity very loosely cupped rolled outward.

Petals: Leathery; with inside satiny; outside satiny.
- *Shape:* Outer: Ovate; with 1 notch. Petals curled back with apex pointed. Intermediate: Ovate; petals curled back with apex pointed. Inner: Ovate; with 1 notch. Petals curled back with apex pointed.

*Color*

This description of a newly opened flower was made from a rose grown outdoors in September 1972 at West Grove, Pa.
- *Outer petal:* Outside surface: 21D. Inside surface: Base and lower part of petal 21B, upper part 52B brushed, penciled and streaked with 20A, 20B and 20C.
- *Intermediate petal:* Outside surface: 21D. Inside surface: Base and lower part of petal 21B, upper part 46D brushed, penciled and streaked with 21B, 21C, and 21D.
- *Inner petal:* Outside surface: 21D. Inside surface: Base and lower part of petal 21B, upper part 46D brushed, penciled and streaked with 21B, 21C, and 21D.

This description was made from a rose that was open for three days outdoors in September, 1972, at West Grove, Pa.
- *Outer petal:* Outside surface: 22D. Inside surface: Base of petal 21B to 21C, upper ⅔ of petal 52B brushed, penciled, streaked with 20B, 20C and 20D.
- *Intermediate petal:* Outside surface: 21D. Inside surface: Base and lower part of petal 21B, upper part 46D, brushed, penciled and streaked with 21D, 21C and 21B.
- *Inner petal:* Outside surface: 22D. Inside surface: Base of petal 21B to 21C, upper ⅔ of petal 52B brushed, penciled, streaked with 20B, 20C and 20D.

General color effect:
- *Newly opened flower:* 22D.
- *Three days open:* Base of petal 21B to 21C, upper ⅔ of petal 52B brushed, penciled, streaked with 20B, 20C, and 20D.

Behavior: Drop off cleanly; slight to 52B and 52C fading; affected by hot weather as follows: Less variegation in colors.

Flower longevity: On bush in garden 3 days in September; cut, grown outdoors, kept at living room temperatures three days in September.

REPRODUCTIVE ORGANS

Stamens: Many; arranged regularly about pistils.
Filaments: Many; most with anthers; medium long.
*Color:* 53B.
Anthers: All open at once; medium large.
Color: 21B.
Occasionally an anther fused with a petaloid.
Pollen: Moderate; gold.
Pistils: Medium.
Styles: Uneven; medium long; thin; bunched colunmar.
Stigma: 20A.
Ovaries: All enclosed in receptacle.
Hips: No hips observed.

PLANT

Foliage:
Leaves: compound of 3, 5, 7 leaflets; normal; medium large; soft, leathery, glossy.
*Leaflets:* shape: oval with apex acute, base obtuse, simply serrate.
*Color:* Mature—Upper surface: 147A; under surface: 147B; Young—Upper surface: 147A; under surface: 147B.
*Rachis:* Medium. Upper side: grooved. Under side: sparsely thorny.

*Stipules:* Medium long; medium wide; with medium points; turning out at an angle of more than 45°.
*Disease:* Resistance comparable to the average variety growing under the same cultural conditions.
Growth:
*Habit:* bushy, much branched.
*Growth:* free.
*Canes:* medium heavy.
*Main stems:* dull; color: 147B. Prickles: several to many; color: 184A. Hairs: none.
*Branches:* Dull; color: 147B. Prickles: several; color: 184A. Hairs: none.
*New Shoots:* dull; color: one side 183A, other side 148B. Prickles: many; color: 184B. Hairs: none.

I claim:

1. A new and distinct variety of rose plant of the Hybrid Tea class, substantially as herein shown and described, characterized particularly as to novelty by being substantially identical with the variety known as Piccadilly (unpatented) except for its flower color, said flower color being deep red with golden stripes, in nearly all petals of each flower, with stripes being of irregular pattern covering more than half of some petals and nil on occasional small petals and petalloids.

No references cited.

ROBERT E. BAGWILL, Primary Examiner